(12) United States Patent
van Eijk et al.

(10) Patent No.: US 9,574,230 B2
(45) Date of Patent: *Feb. 21, 2017

(54) HIGH THROUGHPUT SCREENING OF POPULATIONS CARRYING NATURALLY OCCURING MUTATIONS

(71) Applicant: Keygene N.V., Wageningen (NL)

(72) Inventors: Michael Josephus Theresia van Eijk, Wageningen (NL); Adrianus Johannes van Tunen, Wageningen (NL)

(73) Assignee: KEYGENE N.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,921

(22) Filed: May 26, 2016

(65) Prior Publication Data
US 2016/0258006 A1    Sep. 8, 2016

Related U.S. Application Data

(63) Continuation of application No. 13/972,152, filed on Aug. 21, 2013, now Pat. No. 9,376,719, which is a continuation of application No. 13/447,871, filed on Apr. 16, 2012, now Pat. No. 8,614,073, which is a continuation of application No. 12/088,794, filed as application No. PCT/NL2006/000467 on Sep. 21, 2006, now abandoned.

(60) Provisional application No. 60/721,528, filed on Sep. 29, 2005.

(51) Int. Cl.
C12Q 1/68    (2006.01)

(52) U.S. Cl.
CPC ........... *C12Q 1/6827* (2013.01); *C12Q 1/6855* (2013.01); *C12Q 1/6858* (2013.01); *C12Q 1/6869* (2013.01); *C12Q 1/6874* (2013.01)

(58) Field of Classification Search
CPC ............... C12Q 1/6858; C12Q 1/6869; C12Q 2525/155; C12Q 2537/143; C12Q 2563/155; C12Q 2563/179; C12Q 1/6874
USPC ...................................................... 435/91.2
See application file for complete search history.

(56) References Cited

U.S. PATENT DOCUMENTS

| | | | |
|---|---|---|---|
| 6,248,526 B1 | 6/2001 | Weimer | |
| 7,220,549 B2 | 5/2007 | Buzby | |
| 8,614,073 B2 | 12/2013 | Van Eijk et al. | |
| 2002/0025532 A1 | 2/2002 | Huang et al. | |
| 2004/0053236 A1 | 3/2004 | McCallum et al. | |
| 2004/0086912 A1 | 5/2004 | Luo et al. | |
| 2004/0101835 A1 | 5/2004 | Willis et al. | |
| 2004/0157238 A1 | 8/2004 | Quinn et al. | |
| 2005/0130173 A1 | 6/2005 | Leamon et al. | |
| 2005/0233354 A1 | 10/2005 | Kennedy | |
| 2008/0032287 A1 | 2/2008 | Cantor et al. | |
| 2008/0194418 A1 | 8/2008 | Johnson et al. | |

FOREIGN PATENT DOCUMENTS

| | | |
|---|---|---|
| JP | 2004-502466 | 1/2004 |
| JP | 2004-113241 | 4/2004 |
| JP | 2004-208586 | 7/2004 |
| WO | WO-93/06239 | 4/1993 |
| WO | WO-01/75167 A1 | 10/2001 |

OTHER PUBLICATIONS

Altshuler, et al. "An SNP map of the human genome generated by reduced representation shotgun sequencing", Nature, Sep. 28, 2000, vol. 47, pp. 513-516.
Amos, CI. et al., "DNA Pooling in Mutation Detection with Reference to Sequence Analysis", American Journal of Human Genetics, vol. 66, 2000, pp. 1689-1692.
Church, et al., "Multiplex DNA Sequencing", Research Articles, Science, vol. 240, Apr. 1988, pp. 185-188.
Colbert, T. et al., "High-Throughput Screening for Induced Point Mutations", Plant Physiology (2001) vol. 126, pp. 480-484.
English Translation of the Office Action received in the related Japanese Patent Application No. 2008-533267, mailed Sep. 26, 2012.
English Translation of the Office Action received in the related Japanese Patent Application No. 2009-504137, dated Aug. 22, 2012.
Office Communication received in the related European Patent Application No. 07747276.9, dated Jan. 15, 2013.
Fakhrai-Rad, H. et al., "Prosequencing: An Accurate Detection Platform for Single Nucleotide Polymorphisms", Human Mutation, vol. 19, pp. 479-485 (2002).
First Examination Report in India Appln No. 1142/KOLNP/2008 dated Feb. 17, 2014.
Gruber, et al. "Estimation of single nucleotide polymorphism allele frequency in DNA pools by using Pyrosequencing", Hum Genet (2002), vol. 110, pp. 395-401.
Gupta, et al. "Single nucleotide polymorphisms: A new paradigm for molecular marker technology and DNA polymorphism detection with emphasis on their use in plants", Current Science, Feb. 25, 2001, vol. 80, No. 4 pp. 524-535.
Henikoff, et al. "TILLING. Traditional Mutagenesis Meets Functional Genomics", Plant Physiology, Jun. 2004, vol. 135, pp. 630-636.
Lavebratt, et al., "Pyrosequencing-Based SNP Allele Frequency Estimation in DNA Pools", Human Mutation, vol. 23, pp. 92-97 (2004).

(Continued)

*Primary Examiner* — Cynthia B Wilder
(74) *Attorney, Agent, or Firm* — Foley & Lardner LLP; Sunit Talapatra

(57) ABSTRACT

Disclosed here is a method for the detection of a naturally occurring mutation in a target sequence in one or more members of a population, comprising: providing a plurality of pools of amplification products each comprising the target sequence amplified from genomic DNA of a subset of the one or more members of the population, wherein each pool of the amplification products shares a unique pool identifier; determining the nucleotide sequence of the amplification products using high throughput sequencing; and identifying mutations by clustering/aligning the sequences of the amplified products without the use of an enzyme which recognizes and cuts single nucleotide sequence mismatches and without performing heteroduplex analysis, and identifying the one or more members carrying the mutation using the pool identifier.

20 Claims, 2 Drawing Sheets

(56) References Cited

OTHER PUBLICATIONS

Li et al., "A fast neutron deletion mutagenesis-based reverse genetics system for plants", The Plant Journal, 2001, vol. 27, No. 3, pp. 235-242.
McCallum et al., "Targeting Induced LocalLesions INGenomes (TILLING) for Plant Functional Genomics", Plant Physiology (2000), vol. 123, No. 2, pp. 439-442.
McCallum, et al., "Targeted Screening for Induced Mutations", Nature Biotechnology (Apr. 2000), vol. 18, No. 4, pp. 455-457.
Nair, et al. "PCR-based DNA markers linked to a gall midge resistance gene, Gm4t, has potential for marker-aided selection in rice", Theor Appl Genet (1996), vol. 92, pp. 660-665.
Notice of Opposition to a European Patent in European Patent No. EP 1929039 by the European Patent Office on Sep. 29, 2010.
Qiu, F. et al., "DNA Sequence-Based 'Bar Codes' for Tracking the Origins of Expressed Sequence Tags from a Maize cDNA Library Constructed Using Multiple mRNA Sources", Plant Physiology, 133:475-481, Oct. 2003.
Sood, et al., Method for reverse genetic screening in zebrafish by resequencing and TILLING', Methods, vol. 29, 2006, pp. 220-227.
Stemple, D.L., "TILLING—a high-throughput harvest for functional genomics", Nature Reviews 1 Genetics, vol. 5, pp. 1-6 (Feb. 2004).
Till, et al. "Large-scale discovery of induced point mutations with high-throughput TILLING." Genome Research, Mar. 2003, vol. 13, No. 3, pp. 524-530.
Vandenbussche, et al. "Toward the analysis of the petunia MADS box gene family by reverse and forward transposon insertion mutagenesis approaches: B, C, and D floral organ identify functions require SEPALLATA-like MADS box genes in petunia." The Plant Cell, Nov. 2003, vol. 15, No. 11, pp. 2680-2693.
Vieux, E. F. et al., "Primer Design for PCR and Sequencing in High-Throughput Analysis of SNPs", BioTechniques, vol. 32, pp. S28-S32 (2002).
Wienholds, et al. "Efficient Target-selected mutagenesis in zebrafish." Genome Research, (2003) vol. 13, No. 12, pp. 2700-2707.
Wienholds, et al. "Target-selected gene inactivation in zebrafish", Methods in Cell Biology, 2004, Chapter 4, vol. 77, pp. 69-90.
Wienholds, et al. "Target-Selected Inactivation of the Zebrafish rag1 Gene", Science (2002), vol. 297, pp. 99-102.
Wolford, et al., "High-throughput Snp detection by using Dna pooling and denaturing high performance liquid chromatography (DHPLC)", Human Genetics (2000) vol. 107, pp. 83-487.
Duprat et al., "The Arabidopsis eukaryotic initiation factor (iso) 4E is dispensable for plant growth but required for susceptibility to potyviruses", The Plant Journal, 2002, vol. 32, pp. 927-934.
Epinat et al., "A novel engineered meganuclease induces homologous recombination in yeast and mammalian cells", Nucleic Acids Research, 2003, vol. 31, No. 11, pp. 2952-2962.
Greene et al., "Spectrum of chemically induced mutations from a large-scale reverse-genetic screen in Arabidopsis", Genetics, Jun. 2003, vol. 164, pp. 731-740.
Havre et al., "Targested mutagenesis of DNA using triple helix-forming oligonucleotides linked to psoralen", Proc. Natl. Acad. Sci, Aug. 1993, vol. 90, pp. 7879-7883.
Lloyd et al., "Targeted mutagenesis using zinc-finger nucleases in Arabidopsis", PNAS, Feb. 8, 2005, vol. 102, No. 6, pp. 2232-2237.
Margulies et al., "Genome sequencing in microfabricated high-density picolitre reactors", Nature, 2005, vol. 437, pp. 376-380.
Menda et al., "In silico screening of a saturated mutation library of tomato", The Plant Journal, 2004, vol. 38, pp. 861-872.
Nicaise et al., "The eukaryotic translation initiation factor 4E controls lettuce susceptibility to the potyvirus Lettuce mosaic virus1", Plant Physiology, Jul. 2003, vol. 132, pp. 1272-1282.
Ruffel et al., "A natural recessive resistance gene against potato virus Y in pepper corresponds to the eukaryotic initiation factor 4E (eIF4E)", The Plant Journal, 2002, vol. 32, pp. 1067-1075.
Ruffel et al., "The recessive potyvirus resistance gene pot-1 is the tomato orthologue of the pepper pvr2-eIF4E gene" Mol.Gen.Genetics, 2005, vol. 274, pp. 346-353.
Shendure et al., "Accurate multiplex polony sequencing of an evolved bacterial genome" Science, Sep. 9 2005, vol. 309, pp. 1728-1732.
Stewart et al., "A rapid CTAB DNA isolation technique useful for Rapd fingerprinting and other PCR applications" Biotechniques, 1993, vol. 14, No. 5, pp. 748-750.

*FIGURE 1*

Consensus sequence

|   | C | G | C | G | C | G | T | G | A | T | A | A | T | G | C | G | A | T | T | C | C | G | T | A | G |   |
|---|---|---|---|---|---|---|---|---|---|---|---|---|---|---|---|---|---|---|---|---|---|---|---|---|---|---|
|   |   |   |   |   |   |   |   |   |   |   |   |   |   |   |   |   |   |   |   |   |   |   |   |   |   | A |
|   |   |   |   |   |   |   |   |   |   |   | T |   |   |   |   |   |   |   |   |   |   |   |   |   |   | A |
|   |   |   | G |   |   |   |   |   |   |   |   |   |   |   |   |   |   |   |   |   |   |   |   |   |   |   |
|   |   |   |   |   | T |   |   |   |   |   |   |   |   |   |   |   |   |   |   |   |   |   |   |   |   |   |
|   |   |   |   |   | T |   |   |   |   |   |   |   |   |   |   |   |   | T |   |   |   |   |   |   |   |   |
|   |   |   |   |   | T |   |   |   |   |   |   |   |   |   |   |   |   |   |   |   |   |   |   |   |   |   |
|   |   |   |   |   | T |   |   |   |   |   |   |   |   |   |   |   |   |   |   |   |   |   |   |   |   |   |
|   |   |   |   |   |   |   |   |   |   |   | C |   |   |   |   |   |   |   |   |   |   |   |   |   |   |   |
|   |   |   |   |   |   |   |   |   |   |   | C |   |   | C |   |   |   |   |   |   |   |   |   |   |   |   |
|   |   |   |   |   |   |   |   |   |   |   | C |   |   |   |   |   |   |   |   |   |   |   |   |   |   |   |
|   |   |   |   |   |   |   |   |   |   |   | C |   |   |   |   |   |   |   |   |   | G |   |   |   |   |   |

*FIGURE 2*

Consensus sequence

| Tag sequence | C | G | C | G | C | G | T | G | A | T | A | A | T | G | C | G | A | T | T | C | C | G | T | A | G |   |
|---|---|---|---|---|---|---|---|---|---|---|---|---|---|---|---|---|---|---|---|---|---|---|---|---|---|---|
| GATC (7) |   |   |   |   |   |   |   |   |   |   |   |   |   |   |   |   |   |   |   |   |   |   |   |   |   | A |
| TAAC (8) |   |   |   |   |   |   |   |   |   |   |   | T |   |   |   |   |   |   |   |   |   |   |   |   |   | A |
|   |   |   | G |   |   |   |   |   |   |   |   |   |   |   |   |   |   |   |   |   |   |   |   |   |   |   |
| ACTG (1) |   |   |   |   | T |   |   |   |   |   |   |   |   |   |   |   |   |   |   |   |   |   |   |   |   |   |
| ACTG (1) |   |   |   |   | T |   |   |   |   |   |   |   |   |   |   |   |   |   | T |   |   |   |   |   |   |   |
| GTGC (2) |   |   |   |   | T |   |   |   |   |   |   |   |   |   |   |   |   |   |   |   |   |   |   |   |   |   |
| GTAC (3) |   |   |   |   | T |   |   |   |   |   |   |   |   |   |   |   |   |   |   |   |   |   |   |   |   |   |
| CCTA (4) |   |   |   |   |   |   |   |   |   |   |   | C |   |   |   |   |   |   |   |   |   |   |   |   |   |   |
| CCTA (4) |   |   |   |   |   |   |   |   |   |   |   | C |   |   | C |   |   |   |   |   |   |   |   |   |   |   |
| GAAT (5) |   |   |   |   |   |   |   |   |   |   |   | C |   |   |   |   |   |   |   |   |   |   |   |   |   |   |
| CGGT (6) |   |   |   |   |   |   |   |   |   |   |   | C |   |   |   |   |   |   |   |   |   | G |   |   |   |   |

SEQUENCE LISTING

<160> NUMBER OF SEQ ID NOS: 57

<210> SEQ ID NO 1
<211> LENGTH: 24
<212> TYPE: DNA
<213> ORGANISM: Artificial
<220> FEATURE:
<223> OTHER INFORMATION: Synthetic

<400> SEQUENCE: 1
cacacatggc agcagctgaa atgg				24

<210> SEQ ID NO 2
<211> LENGTH: 24
<212> TYPE: DNA
<213> ORGANISM: Artificial
<220> FEATURE:
<223> OTHER INFORMATION: Synthetic

<400> SEQUENCE: 2
cacagatggc agcagctgaa atgg				24

<210> SEQ ID NO 3
<211> LENGTH: 24
<212> TYPE: DNA
<213> ORGANISM: Artificial
<220> FEATURE:
<223> OTHER INFORMATION: Synthetic

<400> SEQUENCE: 3
cacgaatggc agcagctgaa atgg				24

<210> SEQ ID NO 4
<211> LENGTH: 24
<212> TYPE: DNA
<213> ORGANISM: Artificial
<220> FEATURE:
<223> OTHER INFORMATION: Synthetic

<400> SEQUENCE: 4
cacgtatggc agcagctgaa atgg				24

<210> SEQ ID NO 5
<211> LENGTH: 24
<212> TYPE: DNA
<213> ORGANISM: Artificial
<220> FEATURE:
<223> OTHER INFORMATION: Synthetic

<400> SEQUENCE: 5
cactcatggc agcagctgaa atgg				24

<210> SEQ ID NO 6
<211> LENGTH: 24
<212> TYPE: DNA
<213> ORGANISM: Artificial
<220> FEATURE:
<223> OTHER INFORMATION: Synthetic

<400> SEQUENCE: 6
cactgatggc agcagctgaa atgg				24

<210> SEQ ID NO 7
<211> LENGTH: 24
<212> TYPE: DNA
<213> ORGANISM: Artificial
<220> FEATURE:
<223> OTHER INFORMATION: Synthetic

<400> SEQUENCE: 7
cagacatggc agcagctgaa atgg				24

<210> SEQ ID NO 8

```
<211> LENGTH: 24
<212> TYPE: DNA
<213> ORGANISM: Artificial
<220> FEATURE:
<223> OTHER INFORMATION: Synthetic

<400> SEQUENCE: 8
cagagatggc agcagctgaa atgg                                              24

<210> SEQ ID NO 9
<211> LENGTH: 24
<212> TYPE: DNA
<213> ORGANISM: Artificial
<220> FEATURE:
<223> OTHER INFORMATION: Synthetic

<400> SEQUENCE: 9
cagcaatggc agcagctgaa atgg                                              24

<210> SEQ ID NO 10
<211> LENGTH: 24
<212> TYPE: DNA
<213> ORGANISM: Artificial
<220> FEATURE:
<223> OTHER INFORMATION: Synthetic

<400> SEQUENCE: 10
cagctatggc agcagctgaa atgg                                              24

<210> SEQ ID NO 11
<211> LENGTH: 24
<212> TYPE: DNA
<213> ORGANISM: Artificial
<220> FEATURE:
<223> OTHER INFORMATION: Synthetic

<400> SEQUENCE: 11
cagtcatggc agcagctgaa atgg                                              24

<210> SEQ ID NO 12
<211> LENGTH: 24
<212> TYPE: DNA
<213> ORGANISM: Artificial
<220> FEATURE:
<223> OTHER INFORMATION: Synthetic

<400> SEQUENCE: 12
cagtgatggc agcagctgaa atgg                                              24

<210> SEQ ID NO 13
<211> LENGTH: 24
<212> TYPE: DNA
<213> ORGANISM: Artificial
<220> FEATURE:
<223> OTHER INFORMATION: Synthetic

<400> SEQUENCE: 13
catcgatggc agcagctgaa atgg                                              24

<210> SEQ ID NO 14
<211> LENGTH: 24
<212> TYPE: DNA
<213> ORGANISM: Artificial
<220> FEATURE:
<223> OTHER INFORMATION: Synthetic

<400> SEQUENCE: 14
```

-continued catgcatggc agcagctgaa atgg 24

<210> SEQ ID NO 15
<211> LENGTH: 24
<212> TYPE: DNA
<213> ORGANISM: Artificial
<220> FEATURE:
<223> OTHER INFORMATION: Synthetic

<400> SEQUENCE: 15
ctacgatggc agcagctgaa atgg 24

<210> SEQ ID NO 16
<211> LENGTH: 24
<212> TYPE: DNA
<213> ORGANISM: Artificial
<220> FEATURE:
<223> OTHER INFORMATION: Synthetic

<400> SEQUENCE: 16
ctagcatggc agcagctgaa atgg 24

<210> SEQ ID NO 17
<211> LENGTH: 24
<212> TYPE: DNA
<213> ORGANISM: Artificial
<220> FEATURE:
<223> OTHER INFORMATION: Synthetic

<400> SEQUENCE: 17
ctcacatggc agcagctgaa atgg 24

<210> SEQ ID NO 18
<211> LENGTH: 24
<212> TYPE: DNA
<213> ORGANISM: Artificial
<220> FEATURE:
<223> OTHER INFORMATION: Synthetic

<400> SEQUENCE: 18
ctcagatggc agcagctgaa atgg 24

<210> SEQ ID NO 19
<211> LENGTH: 24
<212> TYPE: DNA
<213> ORGANISM: Artificial
<220> FEATURE:
<223> OTHER INFORMATION: Synthetic

<400> SEQUENCE: 19
ctcgaatggc agcagctgaa atgg 24

<210> SEQ ID NO 20
<211> LENGTH: 24
<212> TYPE: DNA
<213> ORGANISM: Artificial
<220> FEATURE:
<223> OTHER INFORMATION: Synthetic

<400> SEQUENCE: 20
ctcgtatggc agcagctgaa atgg 24

<210> SEQ ID NO 21
<211> LENGTH: 24
<212> TYPE: DNA

```
<213> ORGANISM: Artificial
<220> FEATURE:
<223> OTHER INFORMATION: Synthetic

<400> SEQUENCE: 21
ctctcatggc agcagctgaa atgg                                              24

<210> SEQ ID NO 22
<211> LENGTH: 24
<212> TYPE: DNA
<213> ORGANISM: Artificial
<220> FEATURE:
<223> OTHER INFORMATION: Synthetic

<400> SEQUENCE: 22
ctctgatggc agcagctgaa atgg                                              24

<210> SEQ ID NO 23
<211> LENGTH: 24
<212> TYPE: DNA
<213> ORGANISM: Artificial
<220> FEATURE:
<223> OTHER INFORMATION: Synthetic

<400> SEQUENCE: 23
ctgacatggc agcagctgaa atgg                                              24

<210> SEQ ID NO 24
<211> LENGTH: 24
<212> TYPE: DNA
<213> ORGANISM: Artificial
<220> FEATURE:
<223> OTHER INFORMATION: Synthetic

<400> SEQUENCE: 24
ctgagatggc agcagctgaa atgg                                              24

<210> SEQ ID NO 25
<211> LENGTH: 24
<212> TYPE: DNA
<213> ORGANISM: Artificial
<220> FEATURE:
<223> OTHER INFORMATION: Synthetic

<400> SEQUENCE: 25
ctgcaatggc agcagctgaa atgg                                              24

<210> SEQ ID NO 26
<211> LENGTH: 24
<212> TYPE: DNA
<213> ORGANISM: Artificial
<220> FEATURE:
<223> OTHER INFORMATION: Synthetic

<400> SEQUENCE: 26
ctgctatggc agcagctgaa atgg                                              24

<210> SEQ ID NO 27
<211> LENGTH: 24
<212> TYPE: DNA
<213> ORGANISM: Artificial
<220> FEATURE:
<223> OTHER INFORMATION: Synthetic

<400> SEQUENCE: 27
ctgtcatggc agcagctgaa atgg                                              24
```

<210> SEQ ID NO 28
<211> LENGTH: 24
<212> TYPE: DNA
<213> ORGANISM: Artificial
<220> FEATURE:
<223> OTHER INFORMATION: Synthetic

<400> SEQUENCE: 28
ctgtgatggc agcagctgaa atgg                                    24

<210> SEQ ID NO 29
<211> LENGTH: 26
<212> TYPE: DNA
<213> ORGANISM: Artificial
<220> FEATURE:
<223> OTHER INFORMATION: Synthetic

<400> SEQUENCE: 29
cacaccccca aaatttca acagtg                                    26

<210> SEQ ID NO 30
<211> LENGTH: 26
<212> TYPE: DNA
<213> ORGANISM: Artificial
<220> FEATURE:
<223> OTHER INFORMATION: Synthetic

<400> SEQUENCE: 30
cacagcccca aaatttca acagtg                                    26

<210> SEQ ID NO 31
<211> LENGTH: 26
<212> TYPE: DNA
<213> ORGANISM: Artificial
<220> FEATURE:
<223> OTHER INFORMATION: Synthetic

<400> SEQUENCE: 31
cacgacccca aaatttca acagtg                                    26

<210> SEQ ID NO 32
<211> LENGTH: 26
<212> TYPE: DNA
<213> ORGANISM: Artificial
<220> FEATURE:
<223> OTHER INFORMATION: Synthetic

<400> SEQUENCE: 32
cacgtcccca aaatttca acagtg                                    26

<210> SEQ ID NO 33
<211> LENGTH: 26
<212> TYPE: DNA
<213> ORGANISM: Artificial
<220> FEATURE:
<223> OTHER INFORMATION: Synthetic

<400> SEQUENCE: 33
cactccccca aaatttca acagtg                                    26

<210> SEQ ID NO 34
<211> LENGTH: 26
<212> TYPE: DNA
<213> ORGANISM: Artificial
<220> FEATURE:

```
<223> OTHER INFORMATION: Synthetic

<400> SEQUENCE: 34
cactgcccca aaatttca acagtg                                          26

<210> SEQ ID NO 35
<211> LENGTH: 26
<212> TYPE: DNA
<213> ORGANISM: Artificial
<220> FEATURE:
<223> OTHER INFORMATION: Synthetic

<400> SEQUENCE: 35
cagaccccca aaatttca acagtg                                          26

<210> SEQ ID NO 36
<211> LENGTH: 26
<212> TYPE: DNA
<213> ORGANISM: Artificial
<220> FEATURE:
<223> OTHER INFORMATION: Synthetic

<400> SEQUENCE: 36
cagagcccca aaatttca acagtg                                          26

<210> SEQ ID NO 37
<211> LENGTH: 26
<212> TYPE: DNA
<213> ORGANISM: Artificial
<220> FEATURE:
<223> OTHER INFORMATION: Synthetic

<400> SEQUENCE: 37 cagcaccccca aaatttca acagtg                                         26

<210> SEQ ID NO 38
<211> LENGTH: 26
<212> TYPE: DNA
<213> ORGANISM: Artificial
<220> FEATURE:
<223> OTHER INFORMATION: Synthetic

<400> SEQUENCE: 38
cagctcccca aaatttca acagtg                                          26

<210> SEQ ID NO 39
<211> LENGTH: 26
<212> TYPE: DNA
<213> ORGANISM: Artificial
<220> FEATURE:
<223> OTHER INFORMATION: Synthetic

<400> SEQUENCE: 39 cagtcccca aaatttca acagtg                                           26

<210> SEQ ID NO 40
<211> LENGTH: 26
<212> TYPE: DNA
<213> ORGANISM: Artificial
<220> FEATURE:
<223> OTHER INFORMATION: Synthetic

<400> SEQUENCE: 40
cagtgcccca aaatttca acagtg                                          26
```

```
<210> SEQ ID NO 41
<211> LENGTH: 26
<212> TYPE: DNA
<213> ORGANISM: Artificial
<220> FEATURE:
<223> OTHER INFORMATION: Synthetic

<400> SEQUENCE: 41
catcgcccca aaatttca acagtg                                          26

<210> SEQ ID NO 42
<211> LENGTH: 26
<212> TYPE: DNA
<213> ORGANISM: Artificial
<220> FEATURE:
<223> OTHER INFORMATION: Synthetic

<400> SEQUENCE: 42 catgcccca aaatttca acagtg                                           26

<210> SEQ ID NO 43
<211> LENGTH: 26
<212> TYPE: DNA
<213> ORGANISM: Artificial
<220> FEATURE:
<223> OTHER INFORMATION: Synthetic

<400> SEQUENCE: 43
ctacgcccca aaatttca acagtg                                          26

<210> SEQ ID NO 44
<211> LENGTH: 26
<212> TYPE: DNA
<213> ORGANISM: Artificial
<220> FEATURE:
<223> OTHER INFORMATION: Synthetic

<400> SEQUENCE: 44
ctagccccca aaatttca acagtg                                          26

<210> SEQ ID NO 45
<211> LENGTH: 26
<212> TYPE: DNA
<213> ORGANISM: Artificial
<220> FEATURE:
<223> OTHER INFORMATION: Synthetic

<400> SEQUENCE: 45
ctcaccccca aaatttca acagtg                                          26

<210> SEQ ID NO 46
<211> LENGTH: 26
<212> TYPE: DNA
<213> ORGANISM: Artificial
<220> FEATURE:
<223> OTHER INFORMATION: Synthetic

<400> SEQUENCE: 46
ctcagcccca aaatttca acagtg                                          26

<210> SEQ ID NO 47
<211> LENGTH: 26
<212> TYPE: DNA
<213> ORGANISM: Artificial
<220> FEATURE:
<223> OTHER INFORMATION: Synthetic
```

```
<400> SEQUENCE: 47
ctcgacccca aaatttca acagtg                                          26

<210> SEQ ID NO 48
<211> LENGTH: 26
<212> TYPE: DNA
<213> ORGANISM: Artificial
<220> FEATURE:
<223> OTHER INFORMATION: Synthetic

<400> SEQUENCE: 48
ctcgtcccca aaatttca acagtg                                          26

<210> SEQ ID NO 49
<211> LENGTH: 26
<212> TYPE: DNA
<213> ORGANISM: Artificial
<220> FEATURE:
<223> OTHER INFORMATION: Synthetic

<400> SEQUENCE: 49 ctctcccca aaatttca acagtg                                           26

<210> SEQ ID NO 50
<211> LENGTH: 26
<212> TYPE: DNA
<213> ORGANISM: Artificial
<220> FEATURE:
<223> OTHER INFORMATION: Synthetic

<400> SEQUENCE: 50
ctctgcccca aaatttca acagtg                                          26

<210> SEQ ID NO 51
<211> LENGTH: 26
<212> TYPE: DNA
<213> ORGANISM: Artificial
<220> FEATURE:
<223> OTHER INFORMATION: Synthetic

<400> SEQUENCE: 51
ctgaccccca aaatttca acagtg                                          26

<210> SEQ ID NO 52
<211> LENGTH: 26
<212> TYPE: DNA
<213> ORGANISM: Artificial
<220> FEATURE:
<223> OTHER INFORMATION: Synthetic

<400> SEQUENCE: 52
ctgagcccca aaatttca acagtg                                          26

<210> SEQ ID NO 53
<211> LENGTH: 26
<212> TYPE: DNA
<213> ORGANISM: Artificial
<220> FEATURE:
<223> OTHER INFORMATION: Synthetic

<400> SEQUENCE: 53 ctgcaccca aaatttca acagtg                                           26

<210> SEQ ID NO 54
<211> LENGTH: 26
```

```
<212> TYPE: DNA
<213> ORGANISM: Artificial
<220> FEATURE:
<223> OTHER INFORMATION: Synthetic

<400> SEQUENCE: 54
ctgctcccca aaaattttca acagtg                                              26

<210> SEQ ID NO 55
<211> LENGTH: 26
<212> TYPE: DNA
<213> ORGANISM: Artificial
<220> FEATURE:
<223> OTHER INFORMATION: Synthetic

<400> SEQUENCE: 55
ctgtccccca aaaattttca acagtg                                              26

<210> SEQ ID NO 56
<211> LENGTH: 26
<212> TYPE: DNA
<213> ORGANISM: Artificial
<220> FEATURE:
<223> OTHER INFORMATION: Synthetic

<400> SEQUENCE: 56
ctgtgcccca aaaattttca acagtg                                              26

<210> SEQ ID NO 57
<211> LENGTH: 287
<212> TYPE: DNA
<213> ORGANISM: Lycopersicon esculentum

<400> SEQUENCE: 57
atggcagcag ctgaaatgga gagaacgatg tcgtttgatg cagctgagaa gttgaaggcc         60
gccgatggag gaggaggaga ggtagacgat gaacttgaag aaggtgaaat tgttgaagaa        120
tcaaatgata cggcatcgta tttagggaaa gaaatcacag tgaagcatcc attggagcat        180
tcatggactt tttggtttga taaccctacc actaaatctc gacaaactgc ttggggaagc        240
tcacttcgaa atgtctacac tttctccact gttgaaaatt tttgggg                      287
```

HIGH THROUGHPUT SCREENING OF POPULATIONS CARRYING NATURALLY OCCURING MUTATIONS

CROSS REFERENCE TO RELATED APPLICATIONS

This application is Continuation application of U.S. patent application Ser. No. 13/972,152, filed Aug. 21, 2013, which is a Continuation application of U.S. patent application Ser. No. 13/447,871, filed Apr. 16, 2012, which is a Continuation of U.S. patent application Ser. No. 12/088,794, filed Sep. 8, 2008, which is the U.S. National Phase of International Patent Application No. PCT/NL2006/000467, filed Sep. 21, 2006, published on Apr. 5, 2007 as WO 2007/037678 A2, which claims priority to U.S. Provisional Patent Application No. 60/721,528, filed Sep. 29, 2005. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on May 16, 2016, is named 085342-1100SequenceListing.txt and is 11 KB.

BACKGROUND OF THE INVENTION

Field of the Invention

The present invention, in the fields of molecular biology and genetics relates to improved strategies for identifying mutations in populations, based on the use of high throughput sequencing technologies. The invention further provides for kits that can be applied in the methods.

Description of the Background Art

Populations carrying mutations, either induced or naturally occurring are used in modern genomics research to identify genes affecting traits of importance by reverse genetics approaches. This is in particular applicable for plants and crops of agronomic importance, but such populations are also useful, for other organisms such as yeast, bacteria etc. Other organisms, such as animals, birds, mammals etc can also be used, but these populations are typically more cumbersome to obtain or to control. Nevertheless, it is observed that the invention described herein is of a very general nature, and can be applied also to such organisms.

Mutagenized populations represent complementary tools for gene discovery, as such populations are commonly used to screen known genes for loss-of-function mutations or assessing phenotype changes in organisms with the mutated gene. The rate-limiting step is the screening work associated with identification of, respectively, organisms carrying a mutation in the gene of interest. Below, the principles of such populations and the screening methods are described in more detail and more efficient screening methods are presented which increase the value of these tools for gene-discovery.

A technology that uses mutagenized populations is known as TILLING (Targeted Induced Local Lesions In Genomes) (McCallum et al., Nat. Biotechnol 2000, 18, 455-457, McCallum et al., Plant Physiology, 2000, 123, 439-442; Till et al. Genome Research 2003, 13, 524-530) relies on random introduction of large numbers of mutations (mostly nucleotide substitutions) into the genome by treatment with ethyl methane sulfonate (EMS) or by ionizing radiation (fast neutron bombardment,) (Li et al, The Plant Journal, 2001, 27, 235-42). Every plant in the population carries several hundred (or thousand) mutations, some of which affect normal development, morphology or otherwise confer a phenotype due to loss-of-function (knock-out, knock-down) of one or multiple genes or their regulatory sequences. A TILLING population generally contains a sufficient number of plants to cover all genes with multiple independent mutations (5-20 per gene). A mutagenized plant population used in TILLING therefore usually consist of 3000-10,000 plants and can be used in two ways:

Reverse Genetics

"Reverse Genetics" is the most common way of using TILLING populations. A gene of interest is identified, e.g., by transcript profiling or a candidate gene approach, and the question to be answered is whether this gene affects a particular phenotypic trait of interest. The challenge therefore is to identify one (or several) plants with loss-of-function mutations in this gene. This is commonly performed in a multi-step screening process, typically comprising the following steps:

1. Genomic DNA of a large number of (pooled) M2 plants (e.g., 3072) of the TILLING population is isolated.
2. Pools of equal amounts of DNA from 8 to 32 plants per pool are assembled, with the pooling level depending on the sensitivity of the CEL I screening system (see below). This results in a total of 96- to 384 pooled DNA samples in case of 3072 plants.
3. Labeled PCR primers are used to amplify parts of the gene from all pooled DNAs. Overlapping PCR fragments are used to cover the entire gene (e.g., 3*600 bp PCR fragments are amplified from a 1500 bp gene).
4. Heteroduplexes of the PCR products obtained from the pooled DNA samples are prepared and incubated with CEL I or another enzyme which recognizes and cuts single nucleotide sequence mismatches (e.g., mung bean nuclease, Si nuclease, Surveyor etc.) and the treated samples are resolved on a denaturing (sequencing) gel or by capillary electrophoresis.
5. Pools containing a plant carrying a mutation in the gene are identified by observing bands of digestion products resulting from CEL I treatment.

To identify the plant carrying the mutation, PCRs are repeated on individual DNAs of the plants in the positive pools, followed by bi-directional Sanger sequencing.

Plants harboring a mutation are grown and out-crossed to wild-type to establish causal relationship between the mutation and the observed phenotype change.

The advantage of CEL I screening (steps 3-5 above) is that pre-screening the pooled samples saves costs over sequencing all plants individually by Sanger sequencing.

However, a limitation of CEL I screening is that not all identified mutations affect gene function (e.g., silent substitutions) and this is not known until the PCR products of individual plants in a positive pool are sequenced. Nevertheless, the CEL I mediated screening method is cost-saving compared to sequencing PCR products of all plants separately.

Another limitation is that CEL I screening involves running gels and scoring, a relatively cumbersome process that requires confirmation of mutations from the second strand as gel-patterns are not always clear-cut.

A third disadvantage is that CEL I screening is relatively insensitive to mutation detection at the termini of the PCR product which may lead to some mutations going undetected. Further disadvantages of CEL I are that it has been found that the enzyme is extremely sensitive to reaction conditions such as salt concentrations. This makes that the enzyme can only be used in a limited number of buffers, thereby hampering the broad use of CEL I. Another practical disadvantage associated with the application of CEL I is that the enzyme is not reliable in cutting all mismatched heteroduplexes.

Finally, CEL I screening is incapable of distinguishing missense mutations (which are the most prevalent) from non-sense mutations, causing a great deal of screening work carried out on positive pools without yielding interesting mutations.

Forward Genetics

Plants of the mutagenized population are grown and phenotyped for traits of interest. Plants with an interesting phenotype are then crossed to a wild-type plant to out-cross mutations that are not linked to the phenotype of interest. Finally, the mutated gene responsible for the phenotype of interest is identified by positional cloning (using genetic markers), analogous to mapping QTL in conventional genetic mapping populations (F2, RIL etc). Although theoretically possible, mutagenized populations are not commonly used this way.

The present invention was made in part improve the existing strategies for screening of mutagenized populations. It is an object of the invention to provide efficient methods for screening large populations for the presence of mutations and to improve efficient assessment of the mutations for impact on gene function, i.e., to reduce the amount of effort expended on screening mutations that do not lead to altered gene functions. The present methods were designed to avoid the use of the CEL I enzyme or its equivalents.

SUMMARY OF THE INVENTION

The present inventors found that using high throughput sequencing strategies, the above-mentioned goals were achieved and mutagenized populations, such as TILLING populations, populations wherein mutations have been introduced rising (synthetic) mutagenic or DNA damaging oligonucleotides or, i.e. by Targeted Nucleotide Exchange (TNE) or by Region Targeted Mutagenesis (RTM), or populations that contain naturally occurring mutations such as Single nucleotide polymorphisms (SNPs), small insertions and deletions, and variations in microsatellite repeat number could be efficiently screened for the presence of mutations of interest.

Definitions

In the following description and examples, a number of terms are used. To provide a clear and consistent understanding of the specification and claims, including the scope to be given such terms, the following definitions are provided. Unless otherwise defined herein, all technical and scientific terms used have the same meaning as commonly understood by those of ordinary skill in the art to which this invention belongs. The disclosures of all publications, patent applications, patents and other references are incorporated by reference herein in their entirety.

"TILLING" or "Targeting induced local lesions in genomes" is a general reverse genetic strategy providing an allelic series of induced (point) mutations by random chemical or physical mutagenesis in combination with PCR-based screening to identify point mutations in a region of interest. In TILLING screening, regions of interest are amplified by PCR. Heteroduplexes between wild-type fragments and fragments harboring an induced mutation are formed by denaturing and reannealing PCR products. These heteroduplexes are cleaved by CEL I and cleaved products are resolved. Throughput can be increased by pooling. Following discovery of PCR products harboring sequence differences in a pool, PCR products included in the pool are commonly screened again by Sanger sequencing of individual PCR products, thereby identifying the mutant plant and the exact sequence difference in the mutated gene.

"Mutagenized Population" refers to a population of organisms (usually plants, but other organisms, including animals such as *Drosophila* and mice may be used to create a mutagenized populations; Schimenti et al., 1998, *Genome Research* 8:698-710) that have been subjected to mutagenesis (chemical or physical) to yield a library of mutants. TILLING populations may vary widely in size, and for certain purposes, partial TILLING populations can be used that contain 90, 80 70, 60, 50, 40 30 or even only 20% of the original population. As an alternative to mutagenized populations, populations can be used wherein the population is not mutagenized but comprises sub-populations that contain naturally occurring mutations such as Single nucleotide polymorphisms (SNPs), small insertions and deletions, and variations in microsatellite repeat number. These populations are particularly advantageous when mutagenized populations are not readily accessible (humans) or where already large germplasms are available. See for instance Comai et al., The Plant Journal, 2004, 37, 778-786. Such a population can be used in combination with a 'reference DNA'.

"Targeted Nucleotide Exchange" or "TNE". Targeted nucleotide exchange (TNE) is a process by which a synthetic oligonucleotide, partially complementary to a site in a chromosomal or an episomal gene directs the reversal of a single nucleotide at a specific site. TNE has been described using a wide variety of oligonucleotides and targets. Some of the reported oligonucleotides are RNA/DNA chimeras, contain terminal modifications to impart nuclease resistance.

"Region targeted mutagenesis" or "RTM". Region targeted mutagenesis is a process by which double-strand breaks at a predefined target site in the genomic DNA are artificially created, resulting in repair of the break by one of various available cellular repair mechanisms, mostly leading to mutations at the site of the break. Double-strand breaks may be created by introduction into the cell nucleus of zinc-finger nucleases (e.g. see Lloyd et al., 2005), meganucleases such as I-SceI (Epinat et al., 2003), or triplex-forming oligonucleotides coupled to mutagenic chemical groups (Havre et al., 1993).

"Nucleic acid": A nucleic acid, as used herein, may include any polymer or oligomer of nucleotides with pyrimidine and purine bases, preferably cytosine, thymine (or uracil), adenine and guanine, respectively (See Lehninger, *Principles of Biochemistry, at* 793-800 (Worth Pub. 1982) which is herein incorporated by reference in its entirety for all purposes). Any deoxyribonucleotide, ribonucleotide or peptide nucleic acid component, and any chemical variant thereof, such as those with methylated, hydroxymethylated or glycosylated forms of these bases, and the like, are included. The polymers or oligomers may be heterogeneous or homogeneous in composition, and may be isolated from naturally occurring sources or may be artificially or synthetically produced. A nucleic acid may be DNA or RNA, or a mixture thereof, and may exist permanently or transiently in single-stranded or double-stranded form, including homoduplexes, heteroduplexes, and hybrid states.

"Tagging" refers to the addition of a tag or label to a nucleic acid in order to be able to distinguish it from a second or further nucleic acid. Tagging can be performed, for example, by the addition of a sequence identifier during amplification by using tagged primers or by any other means known in the art. Such a sequence identifier can be a unique base sequence of varying but defined length uniquely used for identifying a specific nucleic acid sample. Typical example are ZIP sequences. Using such a tag, the origin of a sample can be determined upon further processing. In the case of combining processed products originating from different nucleic acid samples, the different nucleic acid samples are generally identified using different tags.

"Tagged library" refers to a library of tagged nucleic acids.

"Sequencing" refers to determining the order of nucleotides (base sequences) in a nucleic acid sample, e.g., DNA or RNA.

"Aligning and alignment" mean the comparison of two or more nucleotide sequences based on the presence of short or long stretches of identical or similar nucleotides. Several methods for alignment of nucleotide sequences are known in the art, as will be further explained below. Sometimes the terms "assembly" or "clustering" are used as synonyms.

"High-throughput screening" (HTS) is a method of scientific experimentation especially relevant to the fields of biology and chemistry. Through a combination of modern robotics and other specialized laboratory hardware, HTS allows an investigator to effectively screen large numbers of samples simultaneously (or virtually simultaneously).

"Primers" in general refers to DNA strands which can prime the synthesis of DNA. DNA polymerase cannot synthesize DNA de novo without primers: it can only extend an existing DNA strand in a reaction in which the complementary strand is used as a template to direct the order of nucleotides to be assembled. The synthetic oligonucleotide molecules which are used in a polymerase chain reaction (PCR) are referred to herein as primers.

"Primers with increased affinity" are primers with modified nucleotides such as PNA or LNA, which increases their thermal stability and allows for allele-specific amplification based on single nucleotide sequence differences. In order to achieve this, one or several modified nucleotides are often included, preferably at the 3'-end of the primer.

"DNA amplification" is typically used to denote the in vitro synthesis of double-stranded DNA molecules using PCR. It is noted that other amplification methods exist and they may also be used in the present invention.

BRIEF DESCRIPTION OF THE DRAWINGS

FIG. 1: Schematic representation of clustered sequences resulting from shotgun sequencing a gene to identify EMS-induced mutations. Mutations are lighter, sequence errors darker colored. Sequence errors are expected to be observed randomly and most often just once.

FIG. 2: Schematic representation of clustered tagged sequencing resulting from a 100 bp gene region amplified with 4 bp-tagged PCR primers from a 3-D pooled library. Mutations are lighter, sequence errors darker colored. Plant IDs are known for mutations identified by 3 tags (1,2,3) and (4,5,6) but not for those identified by less than 2 tag (7,8). Sequence errors are expected to be observed randomly and just once.

DETAILED DESCRIPTION OF THE INVENTION

Figure 3:
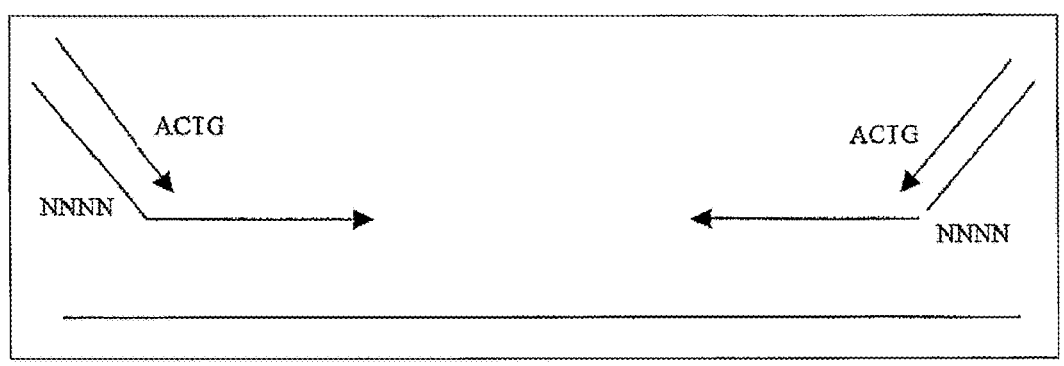
FIG. 3: Illustration of the system of long and short PCR primers to use in tagging the sequences.

In one aspect the invention is directed to a method for the detection of a mutation in a target sequence in a member of a mutagenized population comprising the steps of:
(a) Isolating genomic DNA of each member of the mutagenized population to provide for DNA samples of each member in the population;
(b) pooling the DNA obtained in step (a);
(c) amplifying the target sequence with a pair of (optionally labeled) primers from the DNA pools;
(d) pooling the amplification products of step (c) to create a library of amplification products;
(e) optionally, fragmenting the amplification products in the library;
(f) determining the nucleotide sequence of the products and/or fragments using high throughput sequencing;
(g) identifying mutations by clustering (aligning) the sequences of the fragments;
(h) screening the identified mutations for a modified function of the target sequence;
(i) designing a primer directed to hybridize to the identified mutation;
(j) amplifying the library of step (d) with the primer of step (i) and one of the primers of step (C);
(k) identifying the member(s) carrying the mutation;
(l) optionally, confirming the mutation by amplifying the target sequence from the member(s) of step (k) using the primers of step (c) and determining the sequence of the amplified product.

The isolation of DNA is generally achieved using common methods in the art such as the collection of tissue from a member of the population, DNA extraction (for instance using the Q-Biogene fast DNA kit), quantification and normalization to obtain equal amounts of DNA per sample. As an example, the present invention is illustrated based on a TILLING population of 3072 plants and a gene of 1500 bp.

The pooling of the isolated DNA can for instance be achieved using a 3-dimensional pooling scheme (Vandenbussche et al., 2003, *The Plant Cell*, 15: 2680-93). The pooling is achieved preferably using equal amounts of DNA. The 3D-pooling scheme may comprise 15×15×14, resulting in 44 pools (15+15+14) containing 3072/14=219 or 3072/15=205 different DNA samples per pool. Other pooling schemes can be used.

The pooling step typically serves to identify the plant containing an observed mutation after one round of PCR screening. Pooling of the DNA further serves to normalize the DNAs prior to PCR amplification to provide for a more equal representation in the libraries for sequencing. The additional advantage of the pooling of the DNA is that not all sequences have to be determined separately, but that the pools allow for rapid identification of the sequences of interest, in particular when tagged libraries are used. This facilitates the screening of large or complex populations in particular.

The amplification of the target sequence with a pair of optionally labeled primers from the pools can be achieved by using a set of primers that have been designed to amplify the gene of interest. As stated, the primers may be labeled to visualize the amplification product of the gene of interest.

The amplification products are pooled, preferably in equal or normalized amounts to thereby create a library of amplification products. Exemplary, the complexity of the library will be 3072 plants×1500 bp gene sequence=4.6 Mb sequence.

The amplification products in the library may be randomly fragmented prior to sequencing of the fragments in case the PCR product length exceeds the average length of the sequence traces. Fragmentation can be achieved by physical techniques, i.e., shearing, sonication or other random fragmentation methods. In step (f), at least part, but preferably the entire, nucleotides sequence of at least part of, but preferably of all the fragments contained in the libraries is determined. In certain embodiments, the fragmentation step is optional. For instance, when the read length of the sequencing technique and the PCR fragments length are about the same, there is no need for fragmentation. Also in the case of larger PCR products this may not be necessary if it is acceptable that only part of the PCR product is sequenced for instance in case of 1500 bp PCR product and read length of 400 (from each side) 700 bp remain unsequenced.

The sequencing may in principle be conducted by any means known in the art, such as the dideoxy chain termination method (Sanger sequencing), but this is less preferred given the large number of sequences that have to be determined. It is however preferred and more advantageous that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) *Proc. Natl. Acad. Sci. USA* 101:5488-93, and technologies of Helios, Solexa, US Genomics, etcetera, which are herein incorporated by reference. It is most preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described allows sequencing of 40 million bases in a single run and is 100 times faster and cheaper than competing technology. The sequencing technology roughly consists of 5 steps: 1) fragmentation of DNA and ligation of specific adaptor to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of/enrichment for beads containing amplified ssDNA molecules on their surface 4) deposition of DNA carrying beads in a PicoTiterPlate®; and 5) simultaneous sequencing in at least 100,000 wells by generation of a pyrophosphate light signal. The method will be explained in more detail below.

In a preferred embodiment, the sequencing comprises the steps of:
(a) annealing adapted fragments to beads, with a single adapted fragment being annealed to each bead;
(b) emulsifying the beads in water-in-oil microreactors, each water-in-oil microreactor comprising a single bead;
(c) loading the beads in wells, each well comprising a single bead; and generating a pyrophosphate signal.

In the first step (a), sequencing adaptors are ligated to fragments within the library. The sequencing adaptor includes at least a "key" region for annealing to a bead, a sequencing primer region and a PCR primer region. Thus, adapted fragments are obtained.

In a second step, adapted fragments are annealed to beads, each bead annealing with a single adapted fragment. To the pool of adapted fragments, beads are added in excess as to ensure annealing of one single adapted fragment per bead for the majority of the beads (Poisson distribution).

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PicoTiter™ Plate allowing for simultaneous sequencing of a large amount of fragments.

After addition of enzyme-carrying beads, the sequence of the fragments is determined using pyrosequencing. In successive steps, the PicoTiter™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described in e.g., WO 03/004690, WO 03/054142, WO 2004/069849, WO 2004/070005, WO 2004/070007, and WO 2005/003375 (all in the name of 454 Life Sciences), which are herein incorporated by reference.

The mutations are identified by clustering of the sequenced fragments in the amplified library. Identification of the mutations is achieved by aligning the determined sequences of the fragments of the libraries. The majority of the sequences are wild-type (not mutated) but the induced mutations and occasional sequencing errors are also observed. As the amplification libraries are sequenced with multifold redundancy (typically about 4- to 5-fold redundant), multiple observations of the same sequence change is indicative of a mutation rather than a sequencing error. See FIG. 1.

The clustering provides alignments of the fragments in the amplified library. In this way for each PCR product in the library, a cluster is generated from sequenced fragments, i.e., a contig of the fragments, is build up from the alignment of the sequence of the various fragments obtained from the fragmenting in step (e).

Methods of alignment of sequences for comparison purposes are well known in the art. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) *Computer Appl. in the Biosci.* 8:155-65; and Pearson et al. (1994) *Meth. Mol. Biol.* 24:307-31, which are herein incorporated by reference. Altschul et al. (1994) *Nature Genet.* 6:119-29 (herein incorporated by reference) present a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx.

In the analysis of mutagenized populations, after the mutations have been identified, the identified mutations are assessed for a modified function of the associated gene, for instance the introduction of a stop codon. This assessment is performed on the sequence itself, for example by six-frame translation. Once the interesting mutations have been identified, the mutations are further investigated to identify the associated member of the population.

For each mutation that has been classified as an interesting mutation, an allele specific primer is designed that targets the mutation of interest. Thus, the allele specific primer is then used in combination with one of the primers used in the amplification of the pooled DNA samples (either the reverse or the forward primer). One or both of the primers may be labeled. The set of primers is used to amplify the pools of DNA. The positive pools are identified and the mutant plant is identified. In the above-mentioned 3D pooling scheme, the allele specific PCR with the set of primers to screen the 3D pooled DNA sample plates results in the identification of 3 positive pools (one in each dimension), which specifies the library address of the mutant plant.

In certain embodiments, the allele-specific primers comprise alternative nucleotides such as Locked Nucleic Acids (LNA) or Peptide Nucleic Acids (PNA) to increase their specificity. Such nucleic acids are widely known in the art and are commercially available from a choice of suppliers.

Confirmation of the mutation is achieved by amplification of the target sequence from the identified mutant plant. This amplification is performed with the primers from step (c). The nucleotide sequence of the amplified product is determined and by comparison with the consensus sequence, the mutation is identified. The sequencing is preferably performed Sanger sequencing.

In one aspect the invention pertains to a method for the detection of a mutation in a target sequence in a member of a mutagenized population comprising the steps of:
(a) isolating genomic DNA of each member of the mutagenized population to provide DNA samples of each member in the population;
(b) pooling the DNA obtained in step (a);
(c) amplifying a part or segment of the target sequence with a pair of tagged (optionally labeled) primers from the DNA pools, preferably wherein at least one of the primers comprise a gene-specific section, a tag and a sequence primer binding site;
(d) pooling the amplification products of step (c) to create a library of amplification products;
(d) determining the nucleotide sequence of the amplification products using high throughput sequencing;
(f) identifying mutations by clustering (aligning) the sequences of the fragments;
(g) identifying the member(s) having the mutation using the tags;
(h) optionally, confirming the mutation by amplifying the target sequence from the member(s) of step (g) using the primers of step (c) and determining the sequence of the amplified product.

The isolation of genomic DNA of the members of the mutagenized population and the pooling of the isolated DNA can be carried out essentially as described above.

A part or segment of the target sequence is amplified using a pair of tagged primers that may be labeled. Preferably, for each pool of each dimension, a different primer is used. In the above illustration this means that 44 forward and 44 reverse primers are preferred. Preferably, each of the forward and reverse primers comprises
(i) a sequence primer binding site that can be used in the following sequencing step,
(ii) a tag that serves to link the primer (and the resulting amplification product) to the original member of the population, and
(iii) a gene specific sequence that is capable of annealing to the target sequence of interest (i.e., the gene).

In a typical embodiment the primer has the following order:
5'-Sequence primer binding site-Tag-Gene specific PCR primer sequence-3'

The length of the sequence primer binding site and the gene specific PCR primer sequence are those that are conventional in common PCR use, i.e., independently from about 10 to about 30 bp with a preference for from 15 to 25 bp. Preferably the part or segment of the sequence that is amplified corresponds to a length that can be sequenced in one run using the high throughput sequencing technologies described below. In certain embodiments the part or segment has a length of between about 50 bp to about 500 bp, preferably from about 75 bp to about 300 bp and more preferably between about 90 bp and about 250 bp. As stated above, this length may vary with the sequencing technology employed including those yet to be developed.

By using primers (forward and/or reverse) containing a tag sequence that is unique for each of the primers representing all pool dimensions, the specific plant origin of each tag sequence is known as the sequence primer anneals upstream of the tag and as a consequence, the tag sequence is present in each amplification product. In certain embodiments, both forward and reverse primers are tagged. In other embodiments, only on of the forward or reverse primers is tagged. The choice between one or two tags depends on the circumstances and depends on the read length of the high throughput sequencing reaction and/or the necessity of independent validation. In the case of, e.g., a 100 bp PCR product that is sequenced unidirectionally, only one tag is needed. In the case of a 200 bp PCR product and a 100 bp read-length, double tagging is useful in combination with bi-directional sequencing as it improves efficiency 2-fold. It further provides the possibility of independent validation in the same step. When a 100 bp PCR product is sequenced bi-directionally with two tagged primers, all traces, regardless of orientation, will provide information about the mutation. Hence both primers provide "address information" about which plant contains which mutation.

The tag can be any number of nucleotides, but preferably contains 2, 3, 4 or 5 nucleotides. With 4 nucleotides permuted, 256 tags are possible, whereas 3 nucleotides permuted provide 64 different tags. In the illustration used, the tags preferably differ by >1 base, so preferred tags are 4 by in length. Amplification using these primers results in a library of tagged amplification products.

In certain embodiments, a system of tags can be used wherein the amplification process includes
(1) a long PCR primer comprising (a) a 5'-constant section linked to (b) a degenerate tag section (NNNN) linked to (c) a gene specific section-3' and
(2) a short PCR primer in subsequent amplifications that consists of (a) the 5'-contact section linked to (b) non-degenerate tag section-3' (i.e., a selection amongst NNNN).

The non-degenerate tag section can be unique for each sample, for example, ACTG for sample 1, AATC for sample 2, etc. The short primer anneals to a subset of the long primer. The constant section of the primer can be used as a sequence primer. See FIG. 3.

The library preferably comprises equal, amounts of PCR products from all amplified pools. In the illustrative example, the library contains 3072 plants×100 bp=307 kb sequence to be determined.

The PCR products in the library are subjected to a sequencing process as disclosed above. In particular, the PCR products are attached to beads using the sequence primer binding site that corresponds to the sequence linked to the bead. Thus the present embodiment does not require fragmentation and adapter ligation. Rather, in this embodiment, the adapters have been introduced earlier via the PCR primer design. This improves the reliability of the method. Following the annealing to the beads, sequencing is performed as described above, i.e., (1) emulsification of the beads in water-in-oil microreactors, (2) emulsion PCR to amplify the individual ssDNA molecules on beads; (3) selection of/enrichment for beads containing amplified ssDNA molecules on their surface, (4) transfer of the DNA carrying beads to a PicoTiterPlate®; and (5) simultaneous sequencing in 100,000 wells by a method that generates a pyrophosphate light signal. Typical output is about 200.000× 100-200 by sequences, representing a 66 fold coverage of all PCR products in the library.

Clustering and alignment is performed essentially as described above. The individual plant containing the mutation can be identified using the tags. In the examples, the combination of the 3 tags denotes the positive pools and the consequently the coordinates of the individual plant in the pools.

Confirmation of the mutation by re-sequencing of the PCR product of the identified mutant sample is as described above.

Various pooling strategies can be used with the present invention, examples of which are multidimensional pooling (including 3D pooling) or column-, row- or plate pooling.

High throughput sequencing methods that can be used here are described, for example, in Shendure et al., *Science* 309:1728-32. Examples include microelectrophoretic sequencing, hybridization sequencing/sequencing by hybridization (SBH), cyclic-array sequencing on amplified molecules, cyclic-array sequencing on single molecules, non-cyclical, single-molecule, real-time methods, such as, polymerase sequencing, exonuclease sequencing, or nanopore sequencing.

For optimal results, fragments or amplified products should be sequenced with sufficient redundancy. Redundancy permits distinction between a sequencing error and a genuine possible mutation. In certain embodiments, the redundancy of the sequencing is preferable at least 4, more preferably at least 5, but, as can be seen from the Examples, redundancies of more than 10, preferably more than 25 or even more than 50 are considered advantageous, although not essential for this invention.

Advantages of the methods of the present invention reside inter alia in the fact that mutations can be assessed in silico for their impact on gene function, meaning that a selection is made for the active mutations. Mutations conferring only silent substitutions can be selected against, thereby making the overall process more economical and efficient. This is a particular advantage with regard to the known CEL I based TILLING technology because the majority of CEL I mutations are C/G to T/A transitions, of which only 5% commonly create stop codons (Colbert et al. 2001). The vast majority are missense mutations of reduced interest. Efficient recognition of members in a population with stop codon mutations economizes the process and obviates the need for additional screening of individual members of positive pools.

All mutations can be found with equal probability, irrespective of their position in the PCR product, in particular when the whole target sequence is screened.

The method further avoids the use of CEL I digestion, heteroduplex formation and cumbersome gel scoring. The invention is therefore insensitive to pooling limitations associated with CEL I technology.

The invention further relates to kits that may contain one or more compounds selected form the group consisting of: one or more (labeled) primers for a particular gene or trait, mutation- or allele-specific primers. The kits may further contain beads, sequencing primers, software, descriptions for pooling strategies and other components that are known for kits per se. In certain embodiments, kits are provided that are dedicated to find specific mutations, for instance disease-related mutations.

The invention is now illustrated here in below.

EXAMPLES

Screening a TILLING population can be advanced by using novel high-throughput sequencing methods, such as that of 454 Life Sciences (Margulies et al., 2005) or Polony Sequencing (Shendure et al., 2005). With the current state-of-the-art, 454 Life Sciences technology produces approximately 20 Mb sequence in a single sequencing run. Read lengths are approximately 100 bp per read. Assuming the screening of a population consisting of 3072 plants for mutations in a 1500 bp gene (as described in the above-cited reference in Chapter 2), two approaches are envisaged and described in more detail below.
(1) an approach where the entire 1500 bp gene is investigated for the presence of EMS induced mutations; and
(1) an approach where one or several 100 bp stretches are investigated for the presence of EMS-induced mutations.

Example I

Screening the Entire 1500 by Region

Genomic DNA of 3072 plants of the TILLING population is isolated. A 3-D pooling scheme of equal amounts of DNA per plant is set up (e.g., 15×15×14), resulting in 44 pools (15+15+14=44) containing 3072/14=219 or 3072/15=205 different DNA samples (Vandenbussche et al., supra).

This pooling step serves to permit identification of a plant containing an observed mutation after one round of PCR screening (step 8). Pooling of genomic DNAs further serves to normalize DNAs prior to PCR amplification to increase the probability that all DNAs are represented equally in the sequence library.

The 1500 bp gene is amplified from the pooled DNA samples using 1 pair of unlabelled PCR primers.

Equal amounts of PCR products from all pools wells are pooled to create a pooled PCR products library (complexity 3072 plants×1500 bp=4.6 Mb sequence).

The pooled PCR product library is subjected to shotgun sequencing using conventional technologies (such as those provided by 454 Life Sciences) wherein PCR products are randomly fragmented, amplified on individual beads and sequenced on the bead. Output is approximately 200,000 100 bp sequences, representing 4- to 5-fold coverage of all PCR products in the library).

All sequences are clustered. The majority of sequences are wild-type but EMS-induced mutations (and sequence errors) are observed as well. Since PCR products are sequenced with 4-5 fold redundancy, multiple observations of the same sequence change is indicative of a mutation rather than a sequencing error (FIG. 1).

Mutations are assessed for their impact on gene function such as introduction of a stop-codon.

An allele-specific primer targeting a mutation of interest (with 3' Locked Nucleic Acid; LNA; or Peptide Nucleic Acid; PNA) is designed to be used in combination with either the forward or reverse primer used in step 3 to screen the 3-D pooled DNA sample plate. Allele-specific PCR will result in three positive pools (one of each dimension), which specifies the library address of the mutant plant.

The mutation is confirmed by amplifying the 1500 bp gene using the primers of step 3, followed by (bi-directional) Sanger sequencing.

Example II

Screening 100 bp Stretches 100 by is the Read Length of One 454 Sequence Run

Genomic DNA of 3072 plants of the TILLING population is isolated. A 3-D pooling scheme of equal amounts of DNA per plant is set up (e.g., 15×15×14), resulting in 44 pools (15+15+14=44) containing 3072/14=219 or 3072/15=205 different DNA samples (Vandenbussche et al., supra).

This pooling step serves to permit identification of the plant containing an observed mutation directly from the sequence data. Pooling of genomic DNAs further serves to normalize DNAs prior to PCR amplification to increase the probability that all DNAs are represented equally in the sequence library.

A 100 bp (or 200 bp) region of the gene is amplified from a the pools by PCR using tagged unlabelled PCR primers. This requires 44 forward and 44 reverse primers (one for each pool of each dimension) with the following configuration:

5'-Sequence primer binding site-4 bp Tag-Gene specific primer sequence-3'.

By using tailed forward and reverse primers containing a 4 bp sequence tag that is different for each of the 44 primers representing all pool dimensions, the specific plant origin of each sequence is known as the sequence primer anneals upstream of the tag. Hence the tag sequence in present in each sequence trace. A 4 bp tag allows $4^4$=256 different tags. A 3 bp tag allows 64 different tag sequences—sufficient to distinguish 44 tags—but tag sequences differing by more than 1 base are preferred.

Equal amounts of PCR products from all pools wells are pooled to create a pooled PCR products library (complexity 3072 plants×100 bp=307 kb sequence).

The pooled PCR product library is provided to 454 for sequencing, i.e., PCR products are amplified and sequenced on the beads. Output is approximately 200,000 100 bp sequences, representing 66-fold coverage of all PCR products in the library.

All sequences (from either direction) are clustered; the majority of sequences are wild-type sequences but EMS-induced mutations (and sequence errors) are observed as well. Since PCR products are sequenced with 66 fold redundancy, multiple observations of the same sequence change are indicative of a mutation rather than a sequencing error (FIG. 1).

The coordinates of the individual plant containing the mutation will be known immediately based on the unique combination of 3 tags sequences that occur in the sequence traces harboring the mutation (FIG. 2).

The mutation is confirmed by amplifying the 1500 bp gene using the primers of step 3, followed by (bi-directional) Sanger sequencing.

Example III

Identifying Specific Mutations in a Mutant Library of Tomato

Mutant Library of Tomato

This example describes the screening of a mutant library of tomato by massive parallel sequencing in order to identify point mutations in a specific locus (target gene). The mutant library used is an isogenic library of inbred determinate tomato cultivar M82 consisting of 5075 M2 families derived from EMS mutagenesis treatments. Seeds of each of the 5075 M2 families were stored at 10% RH and 7° C. The origin and characteristics of the library are described in Menda et al. (Plant J. 38: 861-872, 2004).

DNA Isolation

Leaf material was harvested from 5 individual greenhouse-grown plants of each of 3072 M2 families randomly chosen from the library. As any mutation occurring in the library will segregate in a Mendelian fashion in the M2 offspring, the pooling of the leaf material of 5 individual M2 plants reduced the likelihood of overlooking any mutation as a consequence of segregation to less than 0.1%. Genomic DNA was isolated from the pooled leaf material using a modified CTAB procedure described by Stuart and Via (*Biotechniques*, 14: 748-750, 1993). DNA samples were diluted to a concentration of 100 ng/µl in TE (10 mM Tris-HCl pH 8.0, 1 mM EDTA) and stored at −20° C. in 96-well microtitre plates.

3D Pooling of the DNA Samples

The isolated DNA samples were normalized to a concentration of 20 ng/µl and subsequently pooled 4-fold resulting in 768 samples comprised in eight 96-well microtitre plates. Subsequently, these eight microtitre plates were subjected to a 3D pooling strategy, resulting in 28 pools of DNA. The 3D pooling strategy consisted of pooling together all DNAs in three different manners, thus ensuring that each single 4-fold pool occurs only once in an X-coordinate pool, only once in a Y-coordinate pool and only once in a Z-coordinate pool. X-pools were assembled by pooling all DNA samples together per column of eight wells (e.g. AH-11) from all eight microtitre plates, resulting in 12 X-pools. Each X-pool therefore held 8 (wells in a column)×8 (plates)=64 samples of 4-fold pools, representing 256 M2 families. Y-pools were assembled by pooling all DNA samples together per row of twelve wells (e.g. A1-A12) from all eight microtitre plates, resulting in 8 Y-pools. Each Y-pool therefore held 12 (wells in a row)×8 (plates)=96 samples of 4-fold pools, representing 384 M2 families. Z-pools were assembled by pooling all DNA samples together from an entire microtitre plate, resulting in 8 Z-pools. Each Z-pool therefore held 12×8=96 samples of 4-fold pools, representing 384 M2 families.

Target Locus

The target locus in this example was part of the tomato gene for eucaryotic initiation factor 4E (eIF4E). This gene has been shown to be involved in susceptibility to infection of potyviruses in *Arabidopsis* (Duprat et al., Plant J. 32: 927-934, 2002), lettuce (Nicaise et al. Plant Physiol. 132: 1272-1282, 2003) and Solanaceae (Ruffel et al., Plant J. 32: 1067-1075, 2002; Mol. Gen. Genomics 274: 346-353, 2005), and specific mutations in this gene are associated with recessive potyvirus resistance. The mutation screening described in this example was aimed to identify additional mutations in the tomato eIF4E gene as possible sources of new potyvirus resistance. For the tomato eIF4E, only the cDNA sequence was known (NCBI accession numbers AY723733 and AY723734). Using a PCR approach using primers designed on the basis of the cDNA sequence, fragments of the genomic sequence of the eIF4E locus of tomato cultivar Moneyberg were amplified and sequenced. This resulted in a sequence of most of the genomic locus of tomato eIF4E. The locus consists of 4 exons and 3 introns. For the mutation screening, exon 1 of the gene was chosen as the target sequence (SEQ ID 57).

SEQ ID 57: Sequence of exon 1 of tomato Moneyberg eIF4E:

ATGGCAGCAGCTGAAATGGAGAGAACGATGTCGTTTGATGCAGCTGAGAA

GTTGAAGGCCGCCGATGGAGGAGGAGGAGAGGTAGACGATGAACTTGAAG

AAGGTGAAATTGTTGAAGAATCAAATGATACGGCATCGTATTTAGGGAAA

GAAATCACAGTGAAGCATCCATTGGAGCATTCATGGACTTTTTGGTTTGA

TAACCCTACCACTAAATCTCGACAAACTGCTTGGGGAAGCTCACTTCGAA

ATGTCTACACTTTCTCCACTGTTGAAAATTTTTGGGG

Primer Design for Target Locus Amplification

Primers were designed for the PCR amplification of exon 1 of tomato eIF4E. The forward primers were designed to correspond to the ATG start codon of the Open Reading Frame of exon 1, with 5' of the ATG a tag sequence of four bases, providing a unique identifier for each of the 28 pools. At the far 5' end of the forward PCR primers, a 5'-C was added. All primers were phosphorylated at their 5' end to facilitate subsequent ligation of adaptors. The sequence and names of the 28 forward primers are listed in Table 1. The tag sequences are underlined.

TABLE 1

Forward primers, sequences and pool identification for exon 1 amplification.

| name | sequence | 3D pool | SEQ ID # |
|---|---|---|---|
| 061009 | CACACATGGCAGCAGCTGAAATGG | X1 | 1 |
| 061010 | CACAGATGGCAGCAGCTGAAATGG | X2 | 2 |
| 061011 | CACGAATGGCAGCAGCTGAAATGG | X3 | 3 |
| 061012 | CACGTATGGCAGCAGCTGAAATGG | X4 | 4 |
| 061013 | CACTCATGGCAGCAGCTGAAATGG | X5 | 5 |
| 061014 | CACTGATGGCAGCAGCTGAAATGG | X6 | 6 |
| 061015 | CAGACATGGCAGCAGCTGAAATGG | X7 | 7 |
| 061016 | CAGAGATGGCAGCAOCTGAAATGG | X8 | 8 |
| 061017 | CAGCAATGGCAGCAGCTGAAATGG | X9 | 9 |
| 061018 | CAGCTATGGCAGCAGCTGAAATGG | X10 | 10 |
| 061019 | CAGTCATGGCAGCAGCTGAAATGG | X11 | 11 |
| 061020 | CAGTGATGGCAGCAGCTGAAATGG | X12 | 12 |
| 061021 | CATCGATGOCAGCAGCTGAAATGG | Y1 | 13 |
| 061022 | CATGCATGGCAGCAGCTGAAATGG | Y2 | 14 |
| 061023 | CTACGATGGCAGCAGCTGAAATGG | Y3 | 15 |

TABLE 1-continued

Forward primers, sequences and pool identification for exon 1 amplification.

| name | sequence | 3D pool | SEQ ID # |
|---|---|---|---|
| 061024 | CTAGCATGGCAGCAGCTGAAATGG | Y4 | 16 |
| 061025 | CTCACATGGCAGCAGCTGAAATGG | Y5 | 17 |
| 061026 | CTCAGATGGCAGCAGCTGAAATGG | Y6 | 18 |
| 061027 | CTCGAATGGCAGCAGCTGAAATGG | Y7 | 19 |
| 061028 | CTCGTATGGCAGCAGCTGAAATGG | Y8 | 20 |
| 061029 | CTCTCATGGCAGCAGCTGAAATGG | Z1 | 21 |
| 061030 | CTCTGATGGCAGCAGCTGAAATGG | Z2 | 22 |
| 061031 | CTGACATGGCAGCAGCTGAAATGG | Z3 | 23 |
| 061032 | CTGAGATGGCAGCAGCTGAAATGG | Z4 | 24 |
| 061033 | CTGCAATGGCAGCAGCTGAAATGG | Z5 | 25 |
| 061034 | CTGCTATGGCAGCAGCTGAAATGG | Z6 | 26 |
| 061035 | CTGTCATGGCAGCAGCTGAAATGG | Z7 | 27 |
| 061036 | CTGTGATGGCAGCAGCTGAAATGG | Z8 | 28 |

The reverse primers were designed to correspond to basepair position 267 to 287 of exon 1 in the non-coding strand. Again, 5' of the priming part the same series of tag sequences of four bases were included, providing a identifier for each of the 28 pools. At the far 5' end of the reverse PCR primers, a 5'-C was added. All primers were phosphorylated at their 5' end to facilitate subsequent ligation of adaptors. The sequence and names of the 28 reverse primers are listed in Table 2. The tags are underlined.

TABLE 2

Reverse primers sequences and pool identification for exon 1 amplification.

| name | sequence | 3D pool | SEQ ID # |
|---|---|---|---|
| 061037 | CACACCCCCAAAAATTTTCAACAGTG | X1 | 29 |
| 061038 | CACAGCCCCAAAAATTTTCAACAGTG | X2 | 30 |
| 061039 | CACGACCCCAAAAATTTTCAACAGTG | X3 | 31 |
| 061040 | CACGTCCCCAAAAATTTTCAACAGTG | X4 | 32 |
| 061041 | CACTCCCCCAAAAATTTTCAACAGTG | X5 | 33 |
| 061042 | CACTGCCCCAAAAATTTTCAACAGTG | X6 | 34 |
| 061043 | CAGACCCCCAAAAATTTTCAACAGTG | X7 | 35 |
| 061044 | CAGAGCCCCAAAAATTTTCAACAGTG | X8 | 36 |
| 061045 | CAGCACCCCAAAAATTTTCAACAGTG | X9 | 37 |
| 061046 | CAGCTCCCCAAAAATTTTCAACAGTG | X10 | 38 |
| 061047 | CAGTCCCCCAAAAATTTTCAACAGTG | X11 | 39 |
| 061048 | CAGTGCCCCAAAAATTTTCAACAGTG | X12 | 40 |
| 061049 | CATCGCCCCAAAAATTTTCAACAGTG | Y1 | 41 |
| 061050 | CATGCCCCCAAAAATTTTCAACAGTG | Y2 | 42 |

TABLE 2-continued

Reverse primers sequences and pool identification for exon 1 amplification.

| name | sequence | 3D pool | SEQ ID # |
|---|---|---|---|
| 06I051 | CTACGCCCCAAAAATTTTCAACAGTG | Y3 | 43 |
| 061052 | CTAGCCCOCAAAAATTTTCAACAGTG | Y4 | 44 |
| 061053 | CTCACCCCAAAAATTTTCAACAGTG | Y5 | 45 |
| 061054 | CTCAGCCCCAAAAATTTTCAACAGTG | Y6 | 46 |
| 061055 | CTCGACCCCAAAAATTTTCAACAGTG | Y7 | 47 |
| 061056 | CTCGTCCCCAAAAATTTTCAACAGTG | Y8 | 48 |
| 061057 | CTCTCCCCAAAAATTTTCAACAGTG | Z1 | 49 |
| 061058 | CTCTGCCCCAAAAATTTTCAACAGTG | Z2 | 50 |
| 061059 | CTGACCCCAAAAATTTTCAACAGTG | Z3 | 51 |
| 061060 | CTGAGCCCCAAAAATTTTCAACAGTG | Z4 | 52 |
| 061061 | CTGCACCCCAAAAATTTTCAACAGTG | Z5 | 53 |
| 061062 | CTGCTCCCCAAAAATTTTCAACAGTG | Z6 | 54 |
| 061063 | CTGTCCCCAAAAATTTTCAACAGTG | Z7 | 55 |
| 061064 | CTGTGCCCCAAAAATTTTCAACAGTG | Z8 | 56 |

Target Locus Amplification

The exon 1 of the target locus was amplified from the 3D pooled DNAs using the forward and reverse primers described above. For each PCR reaction, a forward and a reverse primer were used with identical tags. For the amplification of exon 1 from each of the 28 3D pools, a different set of forward and reverse primers was used.

The PCR amplification reaction conditions for each sample were as follows:

25 µl DNA (=50 ng); 5 µl RNase-mix; 10 µl 5× Herculase PCR-buffer; 0.6 µl of the four dNTPs (20 mM); 1.25 µl forward primer (50 ng/µl); 1.25 µl reverse primer (50); 0.5 Herculase DNA polymerase; 28.9 µl milliQ-purified water. The RNase-mix consisted of 157.5 milliQ-purified water+ 17.5 µl RNase.

Figure 4:
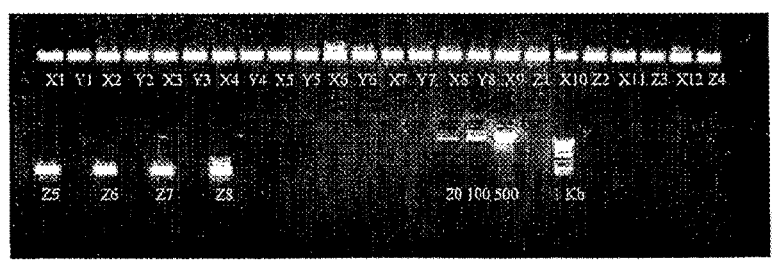
FIG. 4. Agarose gel estimation of the PCR amplification yield of eIF4E exon 1 amplification for each of the 28 3D pools.

PCR amplifications were performed in a PE9600 thermocycler with a gold or silver block using the following conditions: 2 minutes hot-start of 94° C., followed by 35 cycles of 30 sec at 94° C., 30 sec at 53° C., 1 min at 72° C., and a final stationary temperature of 4° C. The PCR amplification efficiency was checked by analysis of 10 µl of PCR products on a 1% agarose gel. FIG. 4 shows the efficient amplification of exon 1 PCR products from each of the 28 3D pools in comparison to a concentration range of lambda DNA on the same gel.

Following amplification, equal amounts of PCR products were mixed and purified using the QIAquick PCR Purification Kit (QIAGEN), according to the QIAquick® Spin handbook (page 18). On each column a maximum of 100 µl of product was loaded. Products were eluted in 10 mM Tris-EDTA.

Sequence Library Preparation and High-Throughput Sequencing

Mixed amplification products from the 3D pools were subjected to high-throughput sequencing on a GS20 sequencer using 454 Life Sciences sequencing technology as described by Margulies et al. (*Nature* 437: 376-380, 2005, and Online Supplements). Specifically, the PCR products were ligated to adaptors to facilitate emulsion-PCR amplification and subsequent fragment sequencing as described by Margulies et al. The 454 adaptor sequences, emulsion PCR primers, sequence primers and sequence run conditions were all as described by Margulies et al. The linear order of functional elements in an emulsion-PCR fragment amplified on Sepharose beads in the 454 sequencing process was as follows:

454 PCR adaptor-454 sequence adaptor-C-nucleotide-4 by tag-target amplification primer sequence 1-target fragment internal sequence-target amplification primer sequence 2-4 by tag-G-nucleotide-454 sequence adaptor-454 PCR adaptor-Sepharose bead.

454 Sequence Run Data-Processing.

After base calling with 454 software for each region of the microtiter plate a file with FASTA formatted sequences was produced. These were concatenated into one file. Within this file a search was conducted with a regular expression to a 100% match of the forward primer preceded with 5 nucleotides (C plus four by tag sequence). The same was done with the reverse primer extended with 5 nucleotides (C plus tag sequence). All sequences were then grouped by their tag sequence (pool indentifiers) in separate files. Each file was analysed with the ssahaSNP tool and the known exon 1 nucleotide sequence as a reference. The ssahaSNP tool reported about all single nucleotide sequence differences and "indels" (single base insertions or deletions as a result of either mutagenesis or erroneous base-calling) of the 454 sequences versus the reference genome. These single nucleotide sequence difference and indel statistics were saved in a database and used for error rate analysis and point mutation identification.

454 Sequencing Error Rate

The total number of correct sequences obtained from the data processing for all 28 pools combined was 247,052. The sequences were divided in two groups, those that aligned with the forward primer and coding strand (5' end) of the exon 1 PCR product (128,594=52%), and those that aligned with the reverse primer and the complementary strand of the PCR product (118,458=48%). The number of sequences obtained from each of the different pools and alignment groups ranged from 69 to 7269. On average, each of the 3072 M2 families should be represented 80 times in the total collection of sequences, and each allele 40 times. Within the alignment group corresponding to the forward primer, 1338 sequences out of 128,594 (1.2%) showed one or more single nucleotide sequence differences in relation to the eIF4E reference sequence along a stretch of 63 bases of aligned target sequence. For the reverse primer group, 743 sequences out of 118,458 (0.6%) showed one or more single nucleotide sequence differences in relation to the eIF4E reference sequence along a stretch of 102 bases of aligned target sequence. Therefore, the single base substitution error rate for both sequence groups combined equals 0.84% for a 165 base stretch, or 0.0051% per base position (0.5 errors per 10,000 bases). This error rate is similar to the one reported by Margulies et al. of 0.004% for individual read substitution errors in test sequences, but much lower than for whole-genome resequencing (0.68%).

A similar analysis of the occurrence of indels in both alignment groups revealed an indel incidence of 3883 (forward primer group) and 3829 (reverse primer group) in a total of 247,052 sequences (is 3.1% in a 165 by stretch). The indel occurrence rate therefore equals 0.01891% per base position (1.89 indels per 10,000 bases). The indel rate is significant higher than the base substitution error rate. Both types of sequencing error combined occur on average at a frequency of 2.39 per 10,000 bases, or 0.024 per base position. This error rate is much lower than reported by Margulies et al., and may be explained by the absence of long homopolymer stretches in the eIF4e exon 1 sequence.

Detection of a Mutation in the Target Locus

Because the objective of this screen is the identification of (EMS)-induced point mutations (preferentially C→T and G→A mutations), all sequences representing indels in comparison to the reference sequence were discarded for the sake of the analysis in this example. Most of the single base substitutions occurred only once in any given 3D pool, some occurred 2 or 3 times, or rarely more often. Since these single base substitutions occur more or less uniformly at every position of the aligned sequence, and at a more or less uniform frequency of 0.005% per base, they were assumed to represent sequencing errors, and not specific mutations that exist in the mutant library. However, at a few specific base positions in the scanned sequence, a much higher incidence of a specific single base sequence difference occurs. Such single base sequence differences reveal mutations in the library, when the following criteria are fulfilled:
1. the single base sequence difference represents an C→T or G→A mutation;
2. the incidence is higher than 20 per 10,000 sequence reads per 3D pool;
3. the single base sequence difference occurs in precisely one and not more than one X-pool, Y-pool and Z-pool.

In this example, one such mutation was found in the alignment group corresponding to the reverse primer, at base position 221 of the eIF4E exon 1 sequence. This mutation, a G→A mutation (corresponding to C→T in the complementary strand) occurred in pool X12 at a frequency of 70 per 10,000 sequences, in pool Y3 at a frequency of 33 per 10,000 and in pool Z6 at 62 per 10,000 sequences. This same mutation at the same position did not occur in any of the other pools, not even at background error rates.

The unique occurrence of this G221A mutation in only the three pools allowed the identification of the original 4-fold pool of DNA, representing four M2 families. DNA of each of these four M2 families was amplified individually with the primers 06F598 and 06F599 that are identical to the forward and reverse primers of Tables 1 and 2, but without the 5' five base sequence tags. The amplified PCR products were subjected to conventional Sanger sequencing. The sequence of the eIF4E gene in one of the four families (coded "24") revealed a dual peak at position 221, corresponding to an overlapping G and A. This is indicative of an M2 family pool, in which half the alleles are wild-type, and the other half carry the G221A point mutation (FIG. 2). The sequences of the other M2 families around base position 221 were according to the reference (wild-type).

The mutation causes an arginine to glutamine substitution. Seeds of this particular M2 family were planted in the greenhouse in order to select for homozygous mutant individuals, that will be used for phenotyping.

In a similar manner, two other point mutations were identified in the 454 sequence reads. An estimation of the mutation density of the M82 tomato mutant library therefore equals 3 mutations per 165 by scanned sequence, or 18 mutations per 1000 bases in 3072 M2 families. This corresponds to mutation densities reported for *Arabidopsis* (Greene et al., *Genetics* 164: 731-740, 2003).

REFERENCES

Colbert et al. 2001. High-throughput screening for induced point mutations. *Plant Physiology* 126: 480-484.
Duprat et al., 2002. The *Arabidopsis* eukaryotic initiation factor (iso)4E is dispensable for plant growth but required for susceptibility to potyviruses. *Plant J.* 32: 927-934.
Epinat et al., 2003. A novel engineered meganuclease induces homologous recombination in yeast and mammalian cells. *Nucleic Acids Research,* 31(11): 2952-2962.
Havre et al., 1993. Targeted mutagenesis of DNA using triple helix-forming oligonucleotides linked to psoralen. *Proc. Natl. AcadSci. USA* 90: 7879-7883.
McCallum et al., 2000. Targeted screening for induced mutations. *Nature Biotechnology* 18: 455-457.
Greene et al., 2003. Spectrum of chemically induced mutations from a large-scale reverse-genetic screen in *Arabidopsis. Genetics* 164: 731-740.
Lloyd et al., 2005. Targeted mutagenesis using zinc-finger nucleases in *Arabidopsis. Proc. NatiAcad. Sci. USA* 102: 2232-2237.
Margulies et al., 2005. Genome sequencing in microfabricated high-density picoliter reactions. *Nature* 437: 376-380.
Menda et al., 2004. In silico screening of a saturated mutation library of tomato. *Plant J.* 38: 861-872.
Nicaise et al., 2003. The eukaryotic translation initiation factor 4E controls lettuce susceptibility to the potyvirus lettuce mosaic virusl. *Plant Physiol.* 132: 1272-1282.
Ruffel et al., 2002. A natural recessive resistance gene against potato virus Y in pepper corresponds to the eukaryotic initiation factor 4E (eIF4E). *Plant J* 32: 1067-1075.
Ruffel et al., 2005. The recessive potyvirus resistance gene pot-1 is the tomato orthologue of the pepper pvr2-eIF4E gene. *Mol. Gen. Genomics* 274: 346-353.
Shendure et al., 2005. Accurate multiplex polony sequencing of an evolved bacterial genome. *Scienceexpress Report*, August 4.
Stuart and Via, 1993. A rapid CTAB DNA isolation technique useful for RAPD fingerprinting and other PCR applications. *Biotechniques,* 14: 748-750.
Vandenbussche et al., 2003. Toward the analysis of the petunia MADS box gene family by reverse and forward transposon insertion mutagenesis approaches: B, C, and D floral organ identity functions require SEPALLATA-like MADS box genes in petunia. *The Plant Cell* 15:2680-2693.

The invention claimed is:

1. A method for the detection of a naturally occurring mutation in a target sequence in one or more members of a population, comprising:
   (a) providing a plurality of pools of amplification products each comprising the target sequence amplified from genomic DNA of a subset of the one or more members of the population, wherein each pool of the amplification products shares a unique pool identifier;
   (b) determining the nucleotide sequence of the amplification products using high throughput sequencing; and
   (c) clustering/aligning the sequences of the amplified products without the use of an enzyme which recognizes and cuts single nucleotide sequence mismatches and without performing heteroduplex analysis, and detecting the one or more members carrying the mutation using the pool identifier.

2. The method according to claim 1, wherein the population comprises sub-populations that comprise naturally occurring mutations.

3. The method according to claim 2, wherein the naturally occurring mutations are selected from the group consisting of single nucleotide polymorphisms, nucleotide insertions and deletions, and variations in microsatellite repeat number.

4. The method according to claim 1, wherein the amplification products are pooled using a 3D-pooling strategy.

5. The method according to claim 1, wherein the high throughput sequencing is performed by Sequencing-by-Synthesis.

6. The method according to claim 1, wherein the high throughput sequencing is performed by pyrosequencing.

7. The method according to claim 1, wherein sequencing is performed on a solid support.

8. The method according to claim 7, wherein the solid support is a bead.

9. The method according to claim 7, wherein sequencing comprises: (i) ligating sequencing adaptors to the amplification products; (ii) annealing the adaptor-ligated products to beads, each bead annealing with a single product; (iii) emulsifying the beads in water-in-oil microreactors such that each microreactor contains a single bead; (iv) performing emulsion PCR to amplify adaptor-ligated products on the surface of the beads; (v) selecting/enriching beads to which are attached the amplified adaptor-ligated products; (vi)

placing the beads in wells such that each well comprises a single bead; and generating a pyrophosphate signal.

10. The method according to claim 1, wherein the target sequence that is amplified is from about 80 to about 400 bp.

11. The method according to claim 1, wherein the target sequence that is amplified is from about 90 to about 300 bp.

12. The method according to claim 1, wherein the target sequence that is amplified is from 100 to about 200 bp.

13. The method according to claim 1, wherein the method further comprises fragmenting the amplification products.

14. The method according to claim 1, wherein step (a) comprises amplifying the target sequence with a pair of optionally labeled or tagged primers.

15. The method according to claim 14, wherein the method further comprises confirming the mutation by amplifying the target sequence from the identified products of step (c) using the primers of step (a) and determining the sequence of the amplified product.

16. The method according to claim 14, wherein at least one of the primers comprises a gene-specific section, a tag and a sequence primer binding site.

17. The method according to claim 1, wherein the amplified products are sequenced with an average redundancy of at least 4.

18. The method according to claim 1, wherein the amplified products are sequenced with an average redundancy of at least 10.

19. The method according to claim 1, wherein the amplified products are sequenced with an average redundancy of at least 25.

20. The method according to claim 1, wherein the amplified products are sequenced with an average redundancy of at least 50.

* * * * *